US008730266B2

(12) United States Patent
Brown et al.

(10) Patent No.: US 8,730,266 B2
(45) Date of Patent: May 20, 2014

(54) SYSTEM AND METHOD FOR INTEGRATING GAZE TRACKING WITH VIRTUAL REALITY OR AUGMENTED REALITY

(75) Inventors: Ian E. Brown, Kingston (CA); Stephen H. Scott, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 472 days.

(21) Appl. No.: 13/128,750

(22) PCT Filed: Nov. 12, 2009

(86) PCT No.: PCT/CA2009/001626
§ 371 (c)(1),
(2), (4) Date: Jun. 23, 2011

(87) PCT Pub. No.: WO2010/054473
PCT Pub. Date: May 20, 2010

(65) Prior Publication Data
US 2012/0038629 A1    Feb. 16, 2012

Related U.S. Application Data

(60) Provisional application No. 61/193,280, filed on Nov. 13, 2008.

(51) Int. Cl.
*G09G 5/00*    (2006.01)
(52) U.S. Cl.
USPC ......................................... 345/633
(58) Field of Classification Search
None
See application file for complete search history.

(56) References Cited

U.S. PATENT DOCUMENTS

| 4,836,670 | A | 6/1989 | Hutchinson |
| 6,152,563 | A | 11/2000 | Hutchinson et al. |
| 6,803,928 | B2 | 10/2004 | Bimber et al. |
| 7,309,128 | B2 | 12/2007 | Cappo et al. |
| 8,040,361 | B2 * | 10/2011 | Bachelder et al. ............ 345/633 |
| 8,294,082 | B2 * | 10/2012 | Melkis et al. ............. 250/227.2 |
| 2006/0210111 | A1 | 9/2006 | Cleveland et al. |

OTHER PUBLICATIONS

Duchowski, et al., "3D Eye Movement Analyisis" Behavior Research Methods, Instruments, and Computers, vol. 34(4), 573-591 (2002).
International Search Report of the International Searching Authority for PCT/CA2009/001626 filed Nov. 12, 2009.
Written Opinion of the International Searching Authority for PCT/CA2009/001626 filed Nov. 12, 2009.

* cited by examiner

*Primary Examiner* — Ryan R Yang
(74) *Attorney, Agent, or Firm* — Stephen J. Scribner

(57) ABSTRACT

This invention relates to gaze tracking methods and systems integrated with virtual reality (VR) or augmented reality (AR). A system may include one or more cameras for capturing images of a subject's eyes, a display device for displaying a VR or AR image, a first reflecting surface associated with the display device for at least partially reflecting light from the eyes to the one or more cameras and for transmitting the VR or AR image; and a second reflecting surface for at least partially reflecting light from the eyes to the one or more cameras and for receiving the VR or AR image and rendering the VR or AR image to the subject as at least one component of a VR or AR environment. The methods and systems described herein may be used in research, medical, industrial, aerospace, and entertainment applications.

31 Claims, 10 Drawing Sheets

SYSTEM AND METHOD FOR INTEGRATING GAZE TRACKING WITH VIRTUAL REALITY OR AUGMENTED REALITY

RELATED APPLICATIONS

This is a 35 U.S.C. 371 national phase of International Application No. PCT/CA2009/001626, filed on 12 Nov. 2009, and claims the benefit of U.S. Provisional Application No. 61/193,280, filed on 13 Nov. 2008, the contents of which are incorporated herein by reference in their entirety.

FIELD OF THE INVENTION

This invention relates generally to gaze tracking methods and apparatus. In particular, this invention relates to gaze tracking methods and apparatus integrated with virtual reality or augmented reality systems.

BACKGROUND OF THE INVENTION

Virtual reality (VR) and augmented reality (AR) are related fields developed in the late $20^{th}$ century that provide an artificial sensory experience to end-users. VR provides a computer generated environment into which a person can immerse oneself and interact with. AR is similar to VR in that it provides a computer generated, immersive environment, but it also includes aspects of the real world as part of the sensory experience (e.g., simultaneous, overlapping views of the real world with computer generated images). VR and AR have found growing use in many different segments of today's society, including entertainment (e.g., video games), research (e.g., neuroscience) and medical applications (e.g., robotic assisted surgery).

As VR and AR have become more accessible, interest has grown amongst a subset of users in combining VR/AR with gaze tracking. Gaze tracking is tracking or monitoring the direction of a person's gaze (i.e., tracking or monitoring where a person is looking). Gaze tracking can provide information about a user's attention, perception, cognition, eye-hand coordination and other neurological functions. Gaze tracking by itself is currently used in scientific research and medical assessment for these purposes, and so these fields have much to gain from the addition of gaze tracking to VR/AR.

SUMMARY OF THE INVENTION

One aspect relates to a gaze tracking system integrated into a mirror-based virtual reality (VR) or augmented reality (AR) system, wherein head fixation is not used, there is no head-mounted gaze tracking equipment, gaze tracking is not affected by the subject's interaction with the VR or AR environment, the gaze tracking equipment does not affect the subject's ability to interact with the VR or AR environment, and the gaze tracking equipment does not affect the subject's view of the VR or AR environment.

According to this aspect, there is provided a virtual reality (VR) or augmented reality (AR) system with gaze tracking of a subject, comprising one or more cameras for capturing images of one or both of the subject's eyes; a display device for displaying a VR or AR image; a first reflecting surface associated with the display device for at least partially reflecting light from the eyes to the one or more cameras and for transmitting the VR or AR image; and a second reflecting surface for at least partially reflecting light from the eyes to the one or more cameras and for receiving the VR or AR image and rendering the VR or AR image to the subject as at least one component of a VR or AR environment.

According to another aspect, a camera and an illuminator (e.g., an IR illuminator), used to monitor gaze direction, are virtually disposed in an ideal location for monitoring gaze direction, rather than being physically disposed in the ideal location. By utilizing a mirror or semi-transparent mirror in a mirror-based VR or AR system, and by adding a beam splitter in front of the VR or AR image producing screen, the camera can capture the eye via reflections in the mirror and beam splitter and likewise the illuminator can illuminate the eye via reflections in the mirror and beam-splitter. For illuminating and viewing the eye, the effect is equivalent to physically disposing the camera and the illuminator in their ideal locations. However, because the camera and the illuminator are not physically disposed in their ideal locations, they do not interfere with, nor are they interfered by, user interaction with the VR or AR environment.

The system may include means to provide information about the subject's interaction with the VR or AR environment. Such means may include a motion capture system, a robotic device with position feedback, a touchscreen, push-buttons, or any other device capable of providing information on the position (i.e., location and/or orientation), motion or interaction of the subject's limbs, or portion thereof, with the VR or AR environment. This information about subject's interaction with the VR or AR environment may be combined with information about gaze direction for research purposes and also for medical applications, for example to detect or assess a brain injury or neurological disorder.

Another aspect provides a virtual reality (VR) or augmented reality (AR) system with gaze tracking of a subject, comprising; one or more illuminators for illuminating one or both of the subject's eyes; one or more cameras for capturing images of one or both of the subject's eyes when illuminated; a display device for displaying a VR or AR image; a first reflecting surface associated with the display device for at least partially reflecting illumination from the one or more illuminators and for transmitting the VR or AR image; a second reflecting surface for at least partially reflecting illumination from the one or more illuminators and for receiving the projected VR or AR image and rendering the VR or AR image to the subject as at least one component of a VR or AR environment; wherein illumination from the one or more illuminators is at least partially reflected by one or both of the first and second reflecting surfaces, and one or both of the subject's eyes; wherein illumination reflected from one or both of the subject's eyes is at least partially reflected by one or both of the first and second reflecting surfaces, and received by the one or more cameras.

In one embodiment, the first reflecting surface may be a beam splitter and the second reflecting surface may be a mirror or a semi-transparent mirror. The one or more illuminators may provide infra-red or near infra-red illumination. At least one illuminator and at least one camera may be located for bright pupil illumination, or they may be located for dark pupil illumination.

The VR or AR image may be a 3-D image or a 2-D image. The VR or AR image may be rendered to the subject below the second reflecting surface. The system may include means for determining and/or recording motion and/or position (i.e., location and/or orientation) of a limb or portion thereof of the subject, while the subject is interacting with the VR or AR environment with the limb or portion thereof. The system may include means for determining and/or recording one or more of motion, location, and orientation of a limb or portion thereof of the subject, while the subject is interacting with the VR or AR environment with the limb or portion thereof. The first reflecting surface and the second reflecting surface may be substantially parallel. The system may include one or more additional beam splitters.

Another aspect provides a method for integrating gaze tracking of a subject with VR or AR, comprising; providing one or more cameras for capturing images of one or both of the subject's eyes; providing a display device for displaying a VR or AR image; disposing a first reflecting surface in association with the display, for at least partially reflecting light from the eyes to the one or more cameras and transmitting the VR or AR image; disposing a second reflecting surface for at least partially reflecting light from the eyes to the one or more cameras and for receiving the projected VR or AR image and rendering the VR or AR image to the subject as at least one component of a VR or AR environment Another aspect provides a method for integrating gaze tracking of a subject with VR or AR, comprising; providing one or more illuminators for illuminating one or both of the subject's eyes; providing one or more cameras for capturing images of one or both of the subject's eyes when illuminated; providing a display device for displaying a VR or AR image; disposing a first reflecting surface in association with the display, for at least partially reflecting illumination from the one or more illuminators and transmitting the VR or AR image; disposing a second reflecting surface for at least partially reflecting illumination from the one or more illuminators and for receiving the projected VR or AR image and rendering the VR or AR image to the subject as at least one component of a VR or AR environment; wherein illumination from the one or more illuminators is at least partially reflected by one or both of the first and second reflecting surfaces, and one or both of the subject's eyes; wherein illumination reflected from one or both of the subject's eyes is at least partially reflected by one or both of the first and second reflecting surfaces, and received by the one or more cameras.

The method may comprise rendering a 3-D VR or AR image, or a 2-D VR or AR image. The method may comprise rendering the VR or AR image to the subject below the second reflecting surface. The method may comprise determining and/or recording motion and/or position of a limb or portion thereof of the subject, while the subject is interacting with the VR or AR environment with the limb or portion thereof. The method may comprise determining and/or recording one or more of motion, location, and orientation of a limb or portion thereof of the subject, while the subject is interacting with the VR or AR environment with the limb or portion thereof. The method may include disposing a second beam splitter associated with one or more cameras and/or one or more illuminators.

Another aspect provides a VR or AR system with gaze tracking of a subject, comprising; one or more illuminators for illuminating one or both of the subject's eyes; one or more cameras for capturing images of the subject's eyes when illuminated; a display device for displaying and projecting a VR or AR image; a reflecting surface for at least partially reflecting illumination from the illuminator and for receiving the projected VR or AR image and rendering the VR or AR image to the subject as at least one component of a VR or AR environment; wherein illumination from the one or more illuminators is at least partially reflected by the reflecting surface and the subject's eye or eyes; wherein illumination reflected from the subject's eye or eyes is at least partially reflected by the reflecting surface and received by the one or more cameras.

In one embodiment the reflecting surface is a mirror or a semi-transparent mirror. In another embodiment the illuminator provides infrared or near infrared illumination. The system may include means for determining and/or recording motion and/or position (i.e., location and/or orientation) of a subject's limb, or portion thereof, while interacting with the VR or AR environment with the limb or portion thereof. The VR or AR image may be 2-D or 3-D.

Another aspect provides a gaze tracking system, comprising: two or more IR illuminators for illuminating the subject's eye or eyes; one or more cameras for capturing images of the subject's eye or eyes when illuminated; means for tracking gaze based on the captured images; a controller for dynamically controlling the illuminators, using an algorithm comprising: monitoring the captured images for IR reflections, e.g. from eye glasses; determining when an IR reflection is interfering with gaze tracking; identifying an IR illuminator that is producing the IR reflection that is causing the interference; and switching the IR illuminators on or off to eliminate IR reflections that interfere with gaze tracking, while retaining enough IR illumination to maintain gaze tracking.

In one embodiment, the gaze tracking system includes a VR or AR system as described herein. The VR or AR system may provide a 2-D or 3-D image.

In one embodiment of the above aspects, illumination from the one or more illuminators is at least partially reflected by the first reflecting surface once and by the second reflecting surface once; and illumination reflected from the subject's eye or eyes is at least partially reflected by the first reflecting surface once and by the second reflecting surface once.

In another embodiment of the above aspects, illumination from the one or more illuminators is at least partially reflected by the first reflecting surface once and by the second reflecting surface twice; and illumination reflected from the subject's eye or eyes is at least partially reflected by the first reflecting surface once and by the second reflecting surface twice.

In another embodiment of the above aspects, illumination from the one or more illuminators is at least partially reflected by the first reflecting surface twice and by the second reflecting surface twice; and illumination reflected from the subject's eye or eyes is at least partially reflected by the first reflecting surface twice and by the second reflecting surface twice.

BRIEF DESCRIPTION OF THE DRAWINGS

For a better understanding of the invention, and to show more clearly how it may be carried into effect, embodiments of the invention will be described below, by way of example, with reference to the accompanying drawings, wherein:

FIG. 2 is a schematic diagram of the effect of baffle design on the IR illuminator's illumination.

FIG. 4 is a schematic diagram showing how ghost images may be produced and the effect of changing the spacing between reflecting surfaces.

FIG. 8 is a schematic diagram showing the different range of gaze angles over which gaze tracking may be carried out for different numbers of reflections.

DETAILED DESCRIPTION OF EMBODIMENTS

Figure 1A:
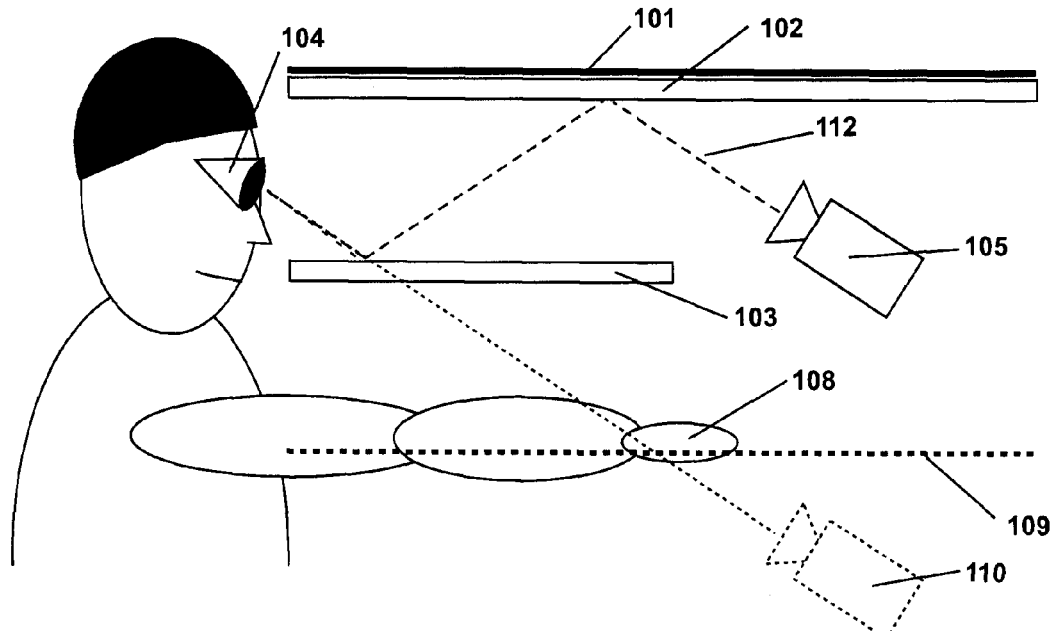
FIGS. 1a and b are schematic diagrams of embodiments in which a remote gaze tracking system is integrated with virtual reality (VR) and/or augmented reality (AR). Both the physical and virtual locations of a camera (FIG. 1a) or camera and illuminator (FIG. 1b) are shown.

In one aspect there is provided a gaze tracking system integrated with a VR or AR system, in which head fixation is not used, nor are any components of the gaze tracking system head-mounted, and in which the desired location of at least part of the gaze tracking system is coincident with a portion of the VR or AR environment over which the subject may interact using one or more limbs, or portion(s) thereof (e.g., with the hands).

As used herein, the term "virtual reality" or "VR" refers to an artificial environment into which a subject may completely or partially immerse him/herself, and/or with which the person may interact. The artificial environment may be provided in 2 or 3 dimensions (i.e., 2-D or 3-D), using any suitable technology. For example, the artificial environment may be computer-generated and adapted (e.g., projected) in a manner that allows the subject to immerse into and/or interact with.

As used herein, the term "augmented reality" or "AR" refers to an artificial environment that includes the features described above for VR, but it also includes aspects of the real world as part of the sensory experience. For example, simultaneous, overlapping views of the real world may be combined with computer-generated images.

In accordance with the aspects described herein, a VR environment or an AR environment may include more than one sensory component. That is, a VR environment or an AR environment may include a visual component, referred to herein as a VR image or an AR image, respectively, and may also include one or more additional components based on other senses, such as an auditory component or a tactile component. For example, a VR or AR environment may include an image (visual component) and push buttons (tactile component).

As used herein, the term "subject" refers to an animal, for example, a mammal, such as a primate, and particularly a human.

As used herein, the term "gaze tracking" refers to tracking or monitoring the direction of a person's gaze (i.e., tracking or monitoring where a person is looking). Gaze tracking may include tracking both the orientation and location of one eye or both eyes with respect to a defined coordinate frame. Hereafter, it will be understood that the term "eye", includes one eye or both eyes of a subject.

Gaze tracking may be accomplished using various approaches, including: tracking the orientation of the eye with respect to the head with both the head position and head orientation fixed; tracking the orientation of the eye with respect to the head along with simultaneous tracking of both the location and orientation of the head; tracking the orientation of the eye in space along with simultaneous tracking of the location of the eye in space (i.e., without head-fixation or head-tracking). The first option may use a head-mounted gaze tracking system or a remote (i.e., non-head-mounted) gaze tracking system; in both cases the gaze tracking system need only track eye-orientation. The second option uses a head-mounted gaze tracking system to track eye-orientation and a separate head-tracking system to track head location and orientation. The third option uses a remote gaze tracking system with both eye orientation tracking and eye location tracking.

Which of the above-mentioned approaches to gaze tracking is used depends on the intended application and the limitations of the approach. The first approach requires head-fixation. A major problem with head fixation is that it has reliability issues that require the subject to be aware of and compensate for. Secondary issues with head fixation are awkwardness, comfort, or other end-user acceptance issues. In basic research head-fixation is often used successfully, but it is generally not appropriate for entertainment or medical assessment. The second approach requires a head-mounted gaze tracking system and some method to track the head. For entertainment uses, most end-users are content to have head-mounted gaze tracking systems. Indeed, for many VR/AR entertainment applications VR/AR is implemented using head-mounted goggles and so head-tracking already occurs. However, there are VR/AR systems that use a non head-mounted mirror or semi-transparent mirror to reflect the visual component of the VR/AR, thus separating the physical location of the display device from the perceived VR/AR image. Such systems are referred to as mirror-based VR/AR, and they do not require any head-mounted equipment or head-tracking equipment. Mirror-based VR/AR is often two-dimensional (2-D), however, with the recent development of three-dimensional (3-D) displays, such as stereoscopic or volumetric displays, mirror-based VR/AR can also provide a 3-D visual experience. VR/AR systems are used in both medical applications and basic research, and in these applications the addition of head-mounted or head-tracking equipment may not be appropriate due to: (i) awkwardness, comfort, or other end-user acceptance issues; (ii) physical space limitations that preclude a head-mounted system; or (iii) increased cost due to additional components (e.g., adding an independent head-tracking system). The process of elimination leads to the use of a remote gaze tracking system with integrated eye-location tracking capabilities as the desired choice for integrating gaze tracking with mirror-based VR/AR.

Remote gaze tracking technologies typically are based on the use of infrared or near infrared illumination (both referred to hereafter as "IR") of the eye. Typically, the IR illumination illuminates the eye and a camera that is sensitive to IR then acquires an image of the eye and/or face and an algorithm on a computer uses the captured image to determine eye orientation. A common approach is for the algorithm to identify and monitor the corneal reflection (CR) and pupil, from which eye orientation is determined. Tracking of eye location may be achieved through various techniques known in the art, such as a 'target' sticker attached to the face near the eye (e.g., Eyelink Remote™, SR Research, Osgoode, ON, Canada), multiple IR illuminators to produce multiple CRs (e.g., iView X RED™, SensoMotoric Instruments GmbH, Berlin, Germany) or multiple cameras (e.g., Smart Eye Pro™, Smart Eye, Gothenburg, Sweden). In all cases, the subject is unaware of the gaze tracking due to the use of invisible IR illumination.

With all of such IR-based gaze tracking technologies, the range of gaze directions that may be tracked is determined primarily by the number of cameras used, with more cameras typically providing an increased range of tracking, and by the location of the IR illuminator(s) and the camera(s) (hereafter referred to in the singular as illuminator and camera). Optimal IR illuminator and camera locations are determined differently for the three degrees of freedom (DOF). A primary issue for all three DOF is that as the angle between the gaze direction and illuminator or camera direction increases, the ability of the gaze tracking system to illuminate or view the eye decreases. Eventually, at a large enough angle gaze tracking fails. Because of this issue, the optimal azimuthal angle (i.e., location in the horizontal plane) is for the illuminator and camera to be near the center of the desired range of gaze tracking angles. For the optimal zenith angle (i.e., location in the vertical plane) the situation is similar, but is confounded by the tendency of the upper eye-lid to droop when looking down, potentially blocking the camera's view of the eye; the optimal zenith angle is slightly below the center of the range of gaze tracking angles. For the third dimension, the minimum distance (i.e., radius) between the eye and the illuminator or camera is determined primarily by the maximal allowable head movement. Larger side-to-side or up-and-down head movements increase the peak angle of the illuminator or camera to the eye, decreasing gaze tracking capabilities; this effect is diminished with increased distance between the eye and the illuminator or camera. Larger allowable front-to-back head movements can create a problem because of changes in illumination intensity. The intensity of illumination drops off with square of the distance from the illuminator. There is a limited range of illumination over which a camera is sensitive enough to capture images appropriate for gaze tracking: if illumination falls outside of this range then gaze tracking can fail. Larger allowable front-to-back head movements increase the relative range of possible illuminations, decreasing gaze tracking capabilities; this effect is diminished with increased distance between the eye and the illuminator.

All of these factors combine to produce a situation with mirror-based VR/AR such that to acquire a maximal range of gaze tracking angles, the optimal location of the IR illuminator and camera typically places the illuminator or camera in a location where they interfere with, or are interfered by, subject interaction in the VR/AR environment. For the azimuthal and zenith angles, the location of the illuminator and camera will usually be coincident with the environment, simply because the environment is the same region over which gaze tracking is desired. For the third dimension (distance from eye), to avoid the problems mentioned above the illuminator and camera typically will be far enough from the eye such that they either block viewing of part of the VR/AR environment, physically block a hand or limb from interacting with the VR/AR environment, or are blocked by a hand or limb interacting with the VR/AR environment. The embodiments described herein avoid such interference.

FIG. 1a shows a first embodiment in which a remote gaze tracking system is integrated with mirror-based VR or AR (hereafter also referred to as "VR/AR"). This embodiment uses light from an external source, such as ambient light, or light from an image producing screen 101, or any other source that can provide sufficient illumination for gaze tracking. The image producing screen 101 is located close to and parallel with a beam splitter 102. As used herein, the term "beam splitter" refers to a substrate that is primarily transparent to light of a given range of wavelengths (e.g., visible light), with at least one surface that reflects light of a different range of wavelengths (e.g., IR). Beam splitters that transmit visible light and reflect IR are also known as hot mirrors. The image producing screen 101 may be, for example, the screen of a back- or front-projection system, the screen of a monitor or television, or the screen of any other display device. The image producing screen 101 may produce either 2-D or 3-D images. The screen 101 and beam splitter 102 are spaced above and parallel with a VR/AR mirror 103. Light 112 reflecting from the subject's eyes is reflected off of the VR/AR mirror 103 and the beam splitter 102 to a camera 105, whereby images of the subject's eye are acquired. The virtual position of the image producing screen image appears to the subject in a plane at 109, if it is a 2-D image, and appears in and/or below the plane 109 if it is a 3-D image. When positioned in front of this arrangement, the subject's limb 108 (e.g., arm) can extend below the VR/AR mirror 103, and the subject's sight line to the limb is through the VR/AR mirror 103, so that the subject can use the limb to interact with the VR or AR environment. The virtual position of the camera appears to the subject as shown at 110.

Figure 1B:
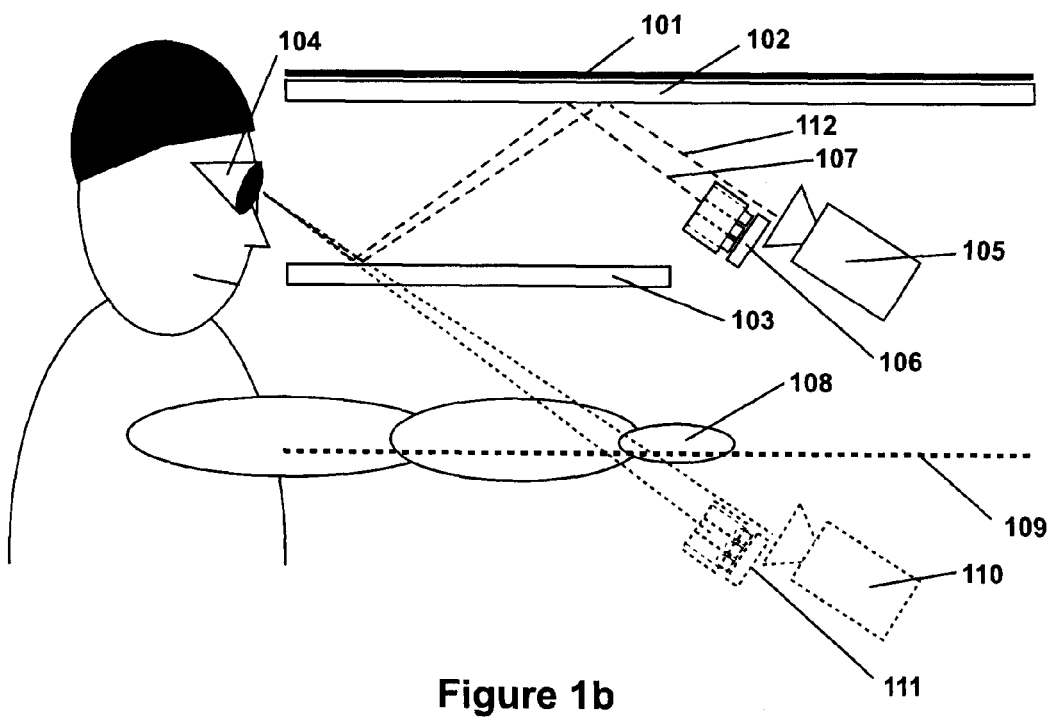

Another embodiment is shown in FIG. 1b. This embodiment is similar to that shown in FIG. 1a, but uses an illuminator 106, such as an IR illuminator, to illuminate the subject's eyes. As in the embodiment of FIG. 1a, the screen 101 and beam splitter 102 are spaced above and parallel with the VR/AR mirror 103. However, in this embodiment an IR illuminator 106 with baffle is aimed at the beam splitter 102 such that IR illumination 107 reflects off the beam splitter and then the VR/AR mirror 103 before reaching the eyes 104 of a subject positioned in front of this arrangement. IR illumination 112 reflecting from the subject's eyes follows this path of reflection in reverse to the camera 105 located close to the illuminator 106, whereby images of the subject's eye are acquired. The virtual position of the image producing screen image appears to the subject in a plane at 109, if it is a 2-D image, and appears in and/or below the plane 109 if it is a 3-D image. When positioned in front of this arrangement, the subject's limb 108 can extend below the VR/AR mirror 103, and the subject's sight line to the limb is through the VR/AR mirror 103, so that the subject can use the limb to interact with the VR or AR environment. The virtual position of the camera and illuminator with baffle appear to the subject as shown at 110 and 111, respectively.

Whereas embodiments may be described herein as using IR illuminators, it will be appreciated that illumination at wavelengths other than IR may also be used. However, IR is invisible to most subjects, and therefore does not distract the subject or interfere with the VR or AR image perceived by the subject.

In the embodiment of FIG. 1b IR illumination is reflected from the upper surface of the VR or AR mirror 103 and the lower surface of the beam splitter 102 disposed just below the image producing screen 101. For both the mirror and the beam splitter this is referred to as first-surface reflection because the reflection occurs on the first surface at which the illumination arrives. A primary IR reflection between the illuminator 106 and the eye occurs once for each of the VR or AR mirror 103 and the beam splitter 102. Similarly, a primary IR reflection between the eye and the camera 105 occurs once for each of the VR or AR mirror 103 and beam splitter 102. All reflecting surfaces are substantially parallel, but they do not need to be horizontal, and they can be disposed at any convenient angle so long as they remain substantially parallel.

For some gaze tracking systems, IR illumination of the eye may occur only via a desired path. For the embodiment shown in FIGS. 1a and b, the desired path uses double reflection as described above. Additional IR illumination via other paths (e.g., direct, single reflection, triple reflection, etc.) is undesired because each path of illumination between the illuminator and the eye has the capacity to create a separate corneal reflection (CR), which potentially causes two problems: (i) possible misidentification of the desired CR; and (ii) partial obscuring of the pupil image, leading to incorrect pupil identification. Although some gaze tracking systems may have an algorithm that can accommodate or account for the effects of simultaneous IR illumination via multiple paths, other systems do not. For eye-tracking systems that require IR illumination of the eye to be via only the desired path, the illuminator may be focused such that it does not provide illumination via the other paths, or illumination via the other paths may be blocked before illuminating the eye. This may be achieved by, for example, the illuminator being provided with a focusing lens to focus the beam of IR illumination, or the illuminator being provided with a baffle to control the beam of IR illumination.

Figure 2A:
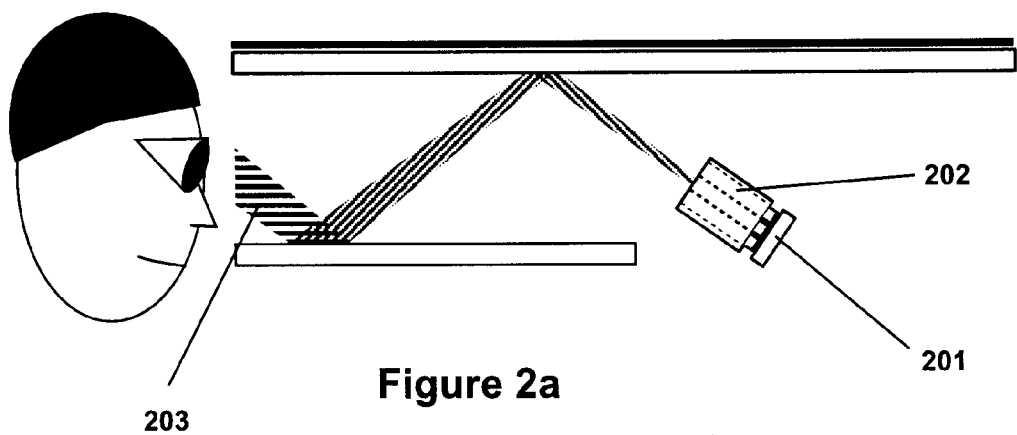
FIGS. 2a, 2b and 2c show the effect of too long, too short, and correct length of baffle for a point-source illuminator.
Figure 2B:
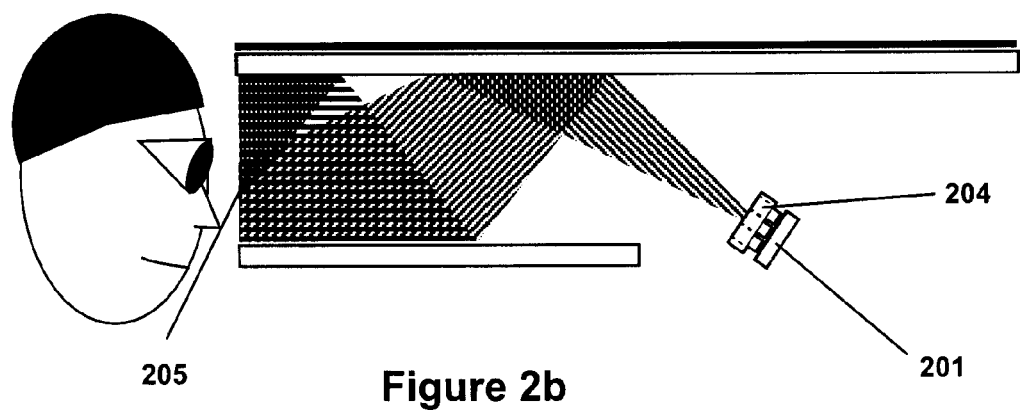
Figure 2C:
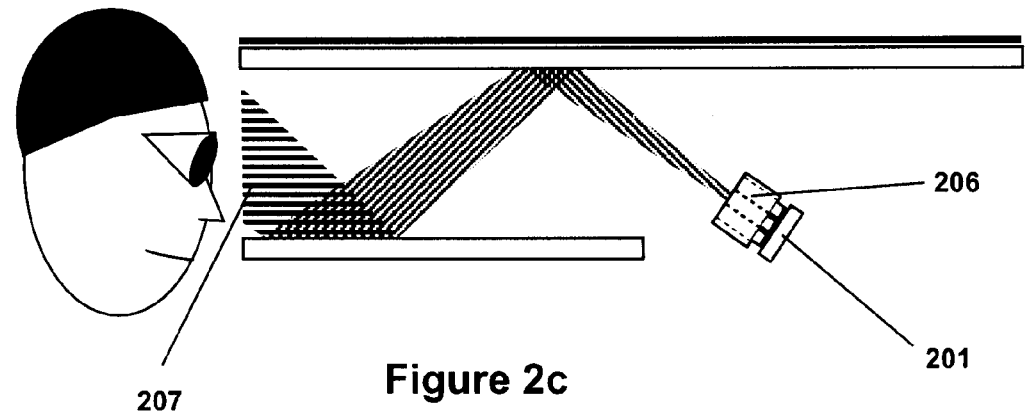

The baffle on the IR illuminator shown in FIG. 1b allows IR illumination via the desired path (e.g., double reflection), and simultaneously prevents illumination via other paths (e.g., direct, single reflection, triple reflection, etc.). For a single source illuminator, the baffle design should be long enough to prevent illumination via unwanted paths (from the entire source), but short enough to allow full illumination from the entire source over the desired range of head movement. FIGS. 2a-c show examples of baffles that are too long (202), too short (204), and of the correct length (206). In particular, if the baffle is too long, illumination can only occur over a narrow path (203), such that illumination only occurs over part of the desired range of head movement. If the baffle is too short, illumination will occur over too broad an area (205), such that the top of the face is illuminated via two or more paths (e.g., double and triple reflections as shown in FIG. 2b) and the bottom of the face is illuminated via two or more pathways (e.g., single and double reflections as shown in FIG. 2b). As stated above, multiple pathways of illumination can lead to multiple CRs which can adversely affect gaze tracking. If the baffle is the correct length, illumination will occur over the entire desired range (207), such that the entire face is illuminated via only one path (e.g., double reflection as shown in FIG. 2c).

Figure 2D:
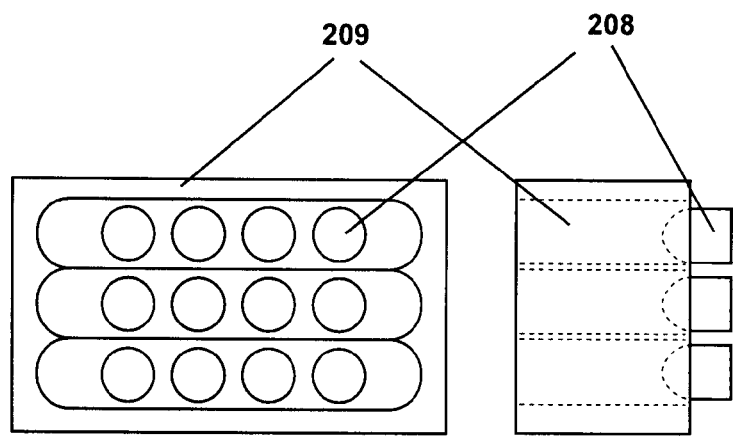
FIG. 2d shows front and side views of a baffle for a 12 IRED illuminator.
Figure 2E:
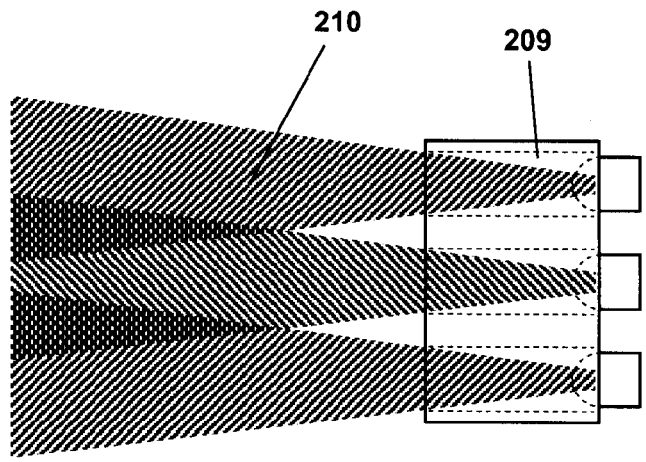
FIGS. 2e and 2f show the effect of different baffle designs on illumination pattern.
Figure 2F:
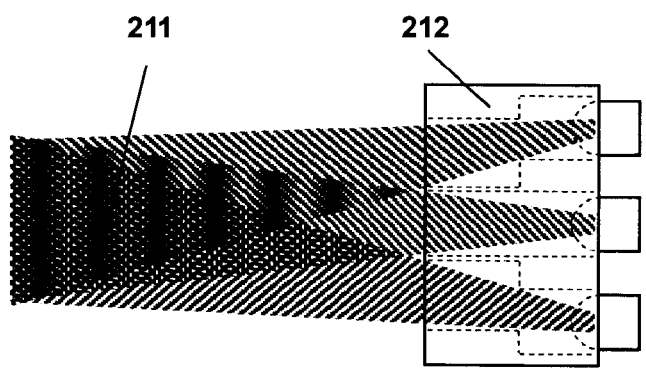

For many IR illuminators, there is more than a single source of IR illumination. With multi-source illuminators the baffle typically needs to be different for different sources. For example, the IR illuminator shown in FIGS. 2d-f contains 12 IR emitting diodes 208 integrated with a baffle 209. In FIG. 2d, the baffle and IR emitting diodes (IREDs) are shown in front and side views on the left and right respectively. Dashed lines indicate hidden edges in the baffle. FIG. 2e shows a side view of the illumination paths 210 for the IREDs. With the baffle 209, the illumination patterns of each row of IREDs are distinct, the illumination pattern produced is non-uniform and it does not drop off abruptly. FIG. 2f shows a different baffle design 212, which provides illumination patterns from the three rows of IREDS that all completely overlap each other, providing a more uniform illumination pattern 211 and more uniform drop off at the top and bottom edges. The faster drop-off provided by baffle design 212 provides maximum illumination over the desired region, with little or no illumination over adjacent undesired regions, so as to avoid illumination via undesirable pathways (e.g., see FIG. 2b).

The embodiments of FIGS. 1a and b may not always be practical because of the commercial availability of semi-transparent mirrors and beam splitters with the desired properties. In particular, the total IR reflectance needs to be high enough to provide enough illumination for the IR camera to acquire a useable image. For example, in the embodiment depicted in FIG. 1b, the amount of IR illumination reaching the face is reduced by the reflections in each mirror, and likewise the amount of facial illumination that reaches the camera is reduced again by the reflections in each mirror. The equation for total IR reflection in the image reaching the camera in this embodiment due to the mirror reflections is:

$$R_{Total} = (R_{Beam\ splitter} * R_{VR/AR})^2 \quad (1)$$

where $R_{Beam\ splitter}$ is the IR reflectance of the beam splitter and $R_{VR/AR}$ is the IR reflectance of the mirror or semi-transparent mirror. In an ideal situation, $R_{Beam\ splitter}$ and $R_{VR/AR}$ would both be close to 1.0 to maximize image brightness. With currently available commercial options, these reflection coefficients are often far less than 1.0.

For AR, a commercially-available option for the VR/AR mirror that provides good visible light transmission/reflection as required for AR, but also has high IR reflectance is Bekaert's Solargard Bronze20™ window film (Bekaert Specialty Films, San Diego, Calif., USA), applied on a glass substrate; it has first surface IR reflectance of $R_{VR/AR} \sim 74\%$. Although beam splitters with first-surface IR reflection >90% IR are available (e.g., from Edmund Optics, Barrington, N.J., USA), due to manufacturing limitations the size of these beam splitters is limited, often to sizes less than about 45×30 cm. To avoid having visible edge effects from the edges of the beam splitter, the beam splitter 102 depicted in FIG. 1b should be the same size or larger than the viewable image on the image producing screen 101. An alternative beam splitter uses a soft-coating on a glass substrate, such as PPG's Solarban 70XL™ (PPG, Pittsburgh, Pa., USA). Although its optical properties are close to ideal as a beam splitter, because it is a soft-coating it cannot be left exposed to typical atmospheric humidity and so it cannot be used for first-surface reflection as in the above embodiment. One of the best first surface beam splitters that is currently available in large sizes (i.e., larger than 45×30 cm) is 3M's Prestige PR70™ window film (3M, St. Paul, Minn., USA), applied to a glass substrate; its first-surface IR reflection coefficient is $R_{Beam\ splitter} \sim 33\%$. Combined with Solargard Bronze20, these two commercially available options give a total reflection according to equation (1) of ~6%. Such substrates, beam splitters and mirrors are of course exemplary and the embodiments described herein are not limited thereto.

While 6% IR reflection might be sufficient for some gaze tracking systems, it may not be sufficient for a high-speed gaze tracking system such as, for example, SR-Research's Eyelink II™. High-speed gaze tracking systems (e.g., 500 Hz) provide increased reliability, particularly in a head-free system (i.e., a system where head position is not fixed), have more accurate timing information, and add the ability to measure gaze velocity. While increasing the strength of IR illumination can increase the illumination reaching the camera, there is a limit above which safety becomes a concern and the subject may get burnt by the IR illumination.

Figure 3:
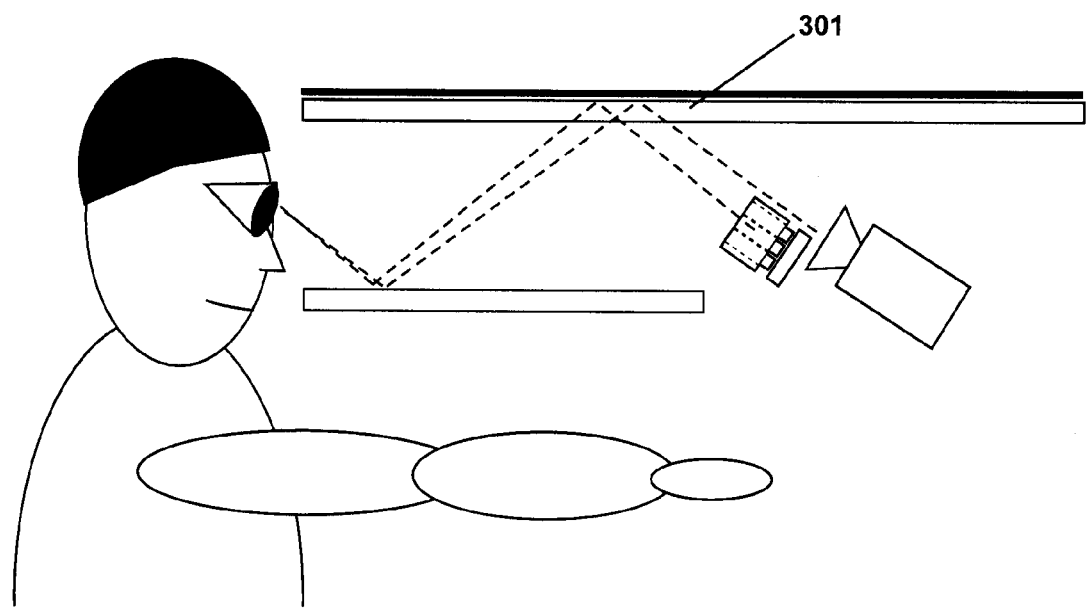
FIG. 3 is a schematic diagram of an embodiment in which a remote gaze tracking system is integrated with VR/AR. In contrast to the embodiment shown in FIG. 1, in this embodiment the reflecting surface of the beam splitter is the second surface.

Another embodiment is shown in FIG. 3. This embodiment is similar to that depicted in FIG. 1b, with the difference that reflection in the beam splitter 301 uses second-surface reflectance. In other words, the illumination is transmitted through the substrate of 301 and reflects off of the upper surface of 301 before being transmitted back through the substrate of 301.

A commercially-available option for beam splitter 301 is 3M's Prestige PR70 window film applied to a low-iron glass substrate such as PPG's Starphire™. PR70 window film has a high IR reflectance when used for $2^{nd}$ surface reflection (~95%). Low-iron glass substrates have higher IR transmission (~95%) compared to standard glass substrates (~75%). PR70 on 6 mm thick Starphire glass provides $R_{Beam\ splitter}$~80%. When combined with Solargard Bronze20 for the VR/AR mirror, the total reflection according to equation (1) is ~35%, or ~6× more than the embodiment depicted in FIG. 1.

Although not shown, a laminated product or an insulated glass unit utilizing a soft-coating such as PPG's Solarban 70XL on Starphire glass, may be used as a beam splitter, with the #2 or #3 surface as the IR reflecting surface. As noted above, such substrates, beam splitters and mirrors are exemplary and the embodiments described herein are not limited thereto.

Figure 4A:
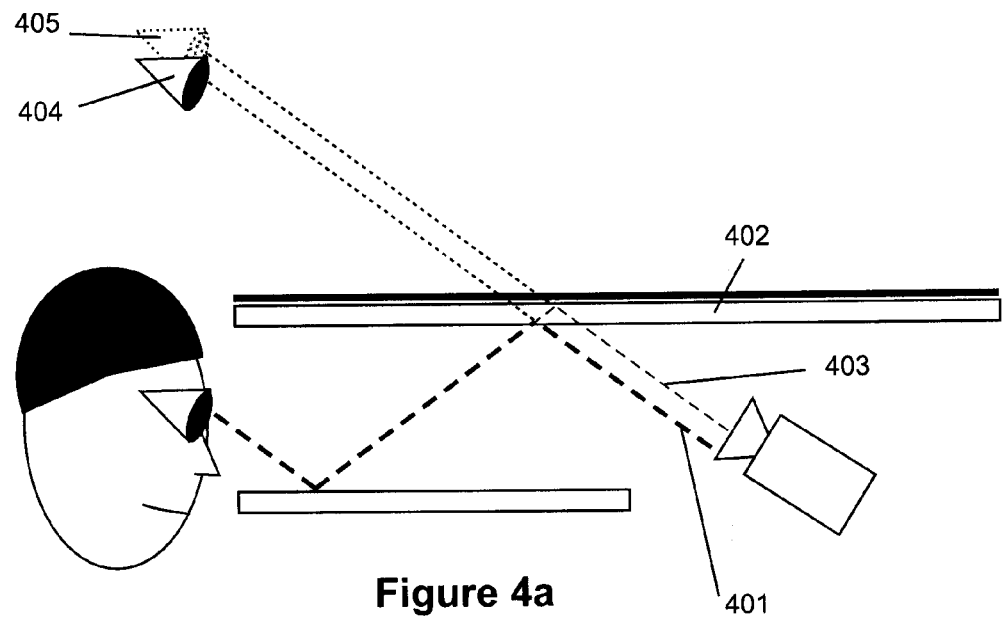
FIG. 4a shows the embodiment of FIG. 1, with the virtual positions of the eye shown as viewed by the camera. Both the primary and ghost images are indicated.

A potential problem with any mirror is that both the first and second surfaces have some finite reflection, so that there are always at least two reflected images. The dimmer, unwanted reflection produces an image that is referred to here as a ghost image. FIG. 4a shows an example wherein the primary reflection 401 occurs off of the first surface of the beam splitter 402 and the secondary reflection 403 occurs off of the second surface of the beam splitter. From the camera's perspective, it views a primary image of the eye 404 and a ghost image of the eye 405, corresponding to the first and second surface reflections, respectively. The ghosting ratio, defined as the relative intensity of the primary or desired reflection to the secondary or undesired reflection, depends on the relative reflectance of the two surfaces and the body transmission of the substrate between the two surfaces, according to the following criteria:

Increasing reflectance of primary reflecting surface increases ghosting ratio

Decreasing reflectance of secondary reflecting surface increases ghosting ratio

Figure 4B:
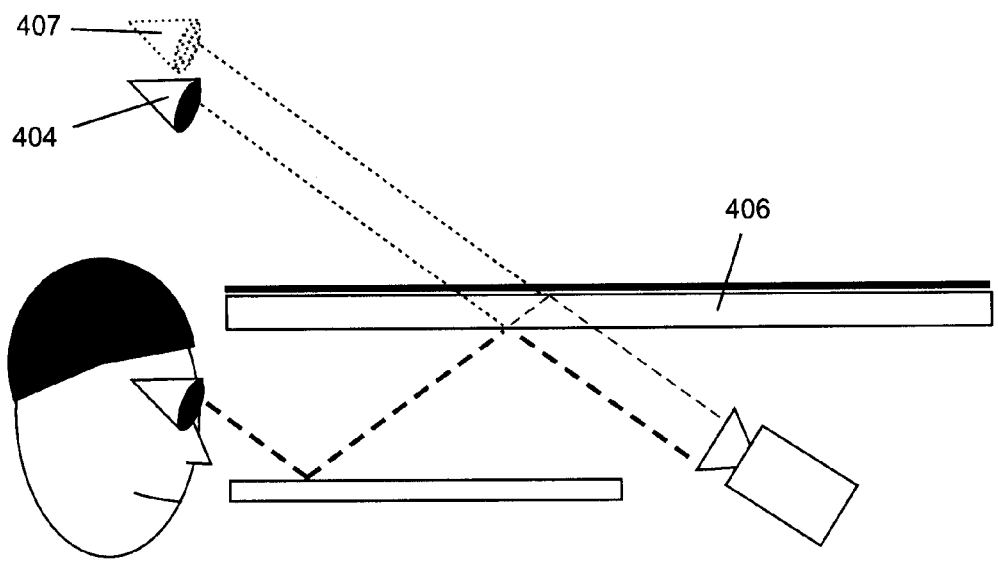
FIG. 4b shows the effect of increasing the spacing between the reflecting surfaces.

If primary reflecting surface is the first surface, then decreasing substrate transmission increases ghosting ratio If primary reflecting surface is the second surface, then increasing substrate transmission increases ghosting ratio For human perception (i.e., visible light), a ghosting ratio of at least 50 is typically needed to not perceive the ghost image. For IR gaze tracking, the primary problem occurs when the ghost image of the CR obscures the pupil in the primary image. If this happens, it may affect the gaze tracking system's ability to correctly identify and locate the pupil. One way to avoid this problem is to have a high enough ghosting ratio so that the ghost image has no effect on the gaze tracking system's ability to correctly identify the pupil. Almost all first-surface reflection beam splitters and mirrors have a high enough ghosting ratio to avoid the problem (e.g., with the PR70 on glass, the ghosting ratio when PR70 is used as a first-surface IR reflector is >4000). In contrast, most second-surface reflection beam splitters and mirrors do not have a high enough ghosting ratio (e.g., with PR70 on low-iron glass, the ghosting ratio when PR70 is used as a second-surface IR reflector is <20). Another way to avoid this problem is to ensure that the ghost CR never enters the pupil over the desired range of gaze tracking. As shown in FIG. 4b, increasing the spacing between the two reflecting surfaces (i.e., increasing the thickness of the beam splitter 406) increases the distance between the primary image 404 and the ghost image 407.

Figure 5A:
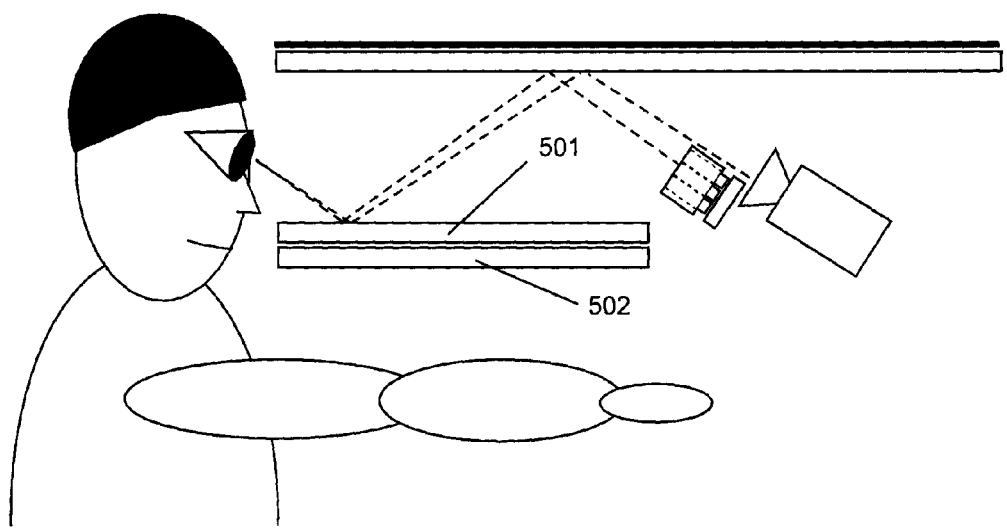
FIG. 5 is a schematic diagram of two embodiments in which a remote gaze tracking system is integrated with VR/AR. In contrast to the embodiment shown in FIG. 1, the embodiment in FIG. 5a uses an IR reflecting surface above the VR/AR mirror.
In FIG. 5b the IR reflecting surface is below the VR/AR mirror.
Figure 5B:
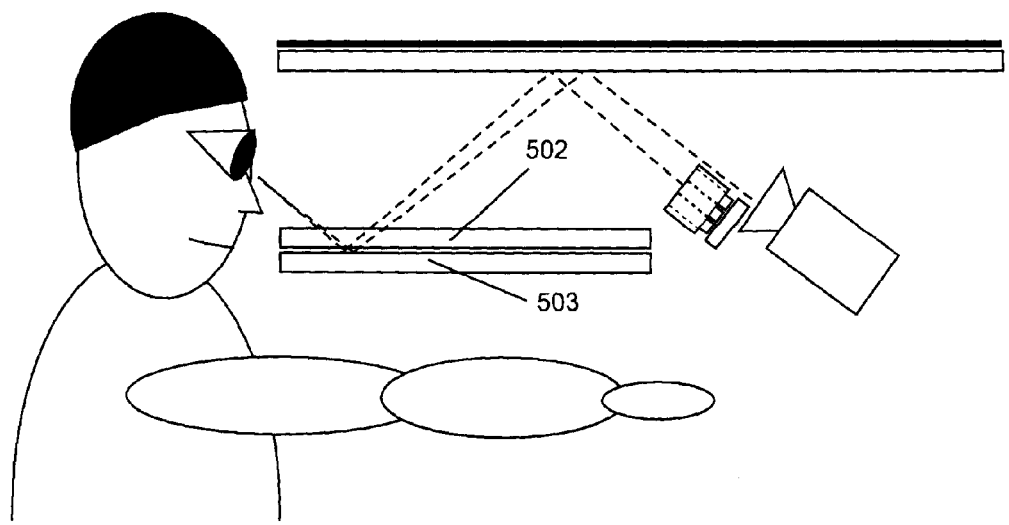

Another embodiment is shown in FIG. 5. It is similar to the embodiment depicted in FIG. 1b, however the reflecting surface of the VR/AR mirror is not used for IR reflection; instead another surface is used. As shown in FIG. 5a, this other surface may be a surface of a beam splitter 501, placed above the VR/AR mirror 502. The IR reflecting surface may be the first surface of the beam splitter 501, as shown in FIG. 5a, or the second surface of the beam splitter 501 (not shown). As shown in FIG. 5b, a beam splitter 503 may be placed below the VR/AR mirror 502. Again, the IR reflecting surface may be the first surface of the beam splitter 503, as shown in FIG. 5b, or the second surface of the beam splitter 503 (not shown). Another option is to have the $2^{nd}$ surface of the VR/AR mirror be the IR reflecting surface (not shown). Issues that may occur with this embodiment include extra ghosting images. If the beam splitter is placed above the VR/AR mirror as in FIG. 5a, then visible ghosting images may occur, affecting the subject's perception of the VR/AR image. This problem may be mitigated by adding an anti-reflective coating. If the IR reflecting surface is below the VR/AR first surface, as shown in FIG. 5b, then IR ghost images may occur. Solutions for that problem were discussed above.

Figure 6A:
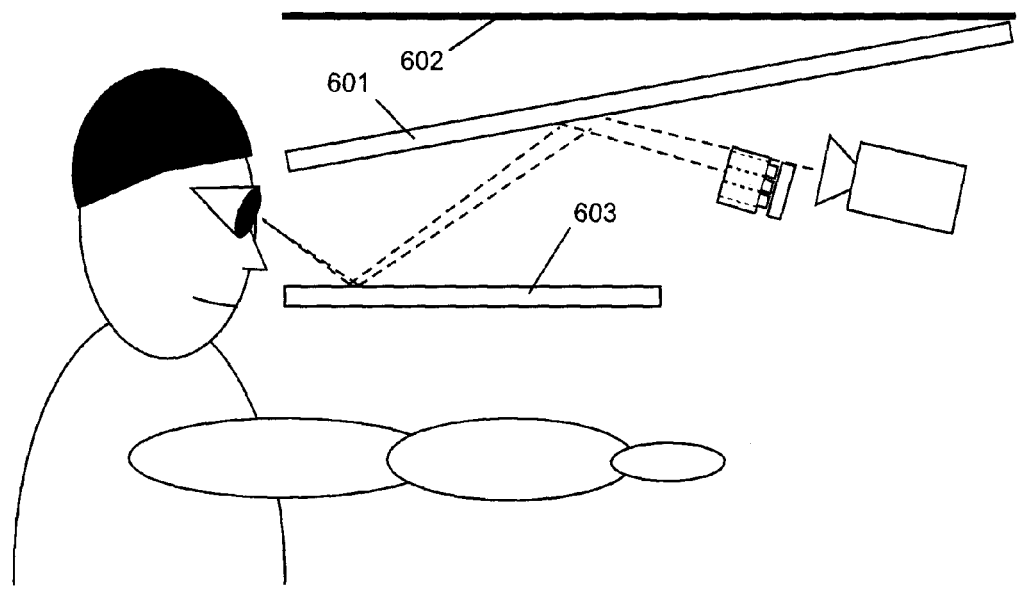
FIG. 6 shows schematic diagrams of two embodiments in which a remote gaze tracking system is integrated with VR/AR. In contrast to the embodiment shown in FIG. 1, the embodiment in FIG. 6a uses a beam splitter that is not parallel to the image producing screen or VR/AR mirror. In the embodiment depicted in FIG. 6b the image producing screen and VR/AR mirror are not parallel.
Figure 6B:
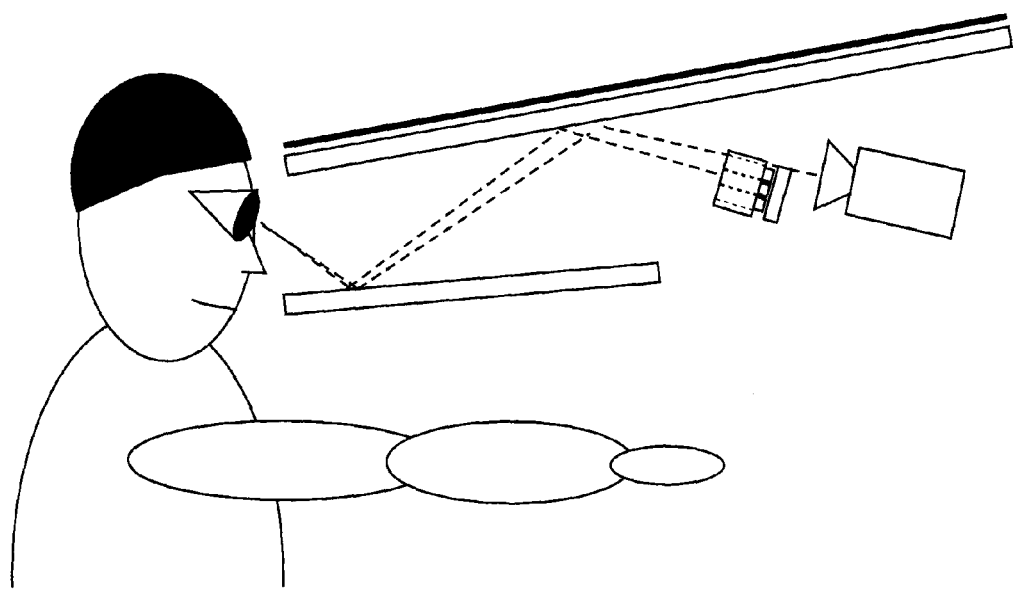

Two more embodiments, shown schematically in FIG. 6 are substantially similar to the embodiment depicted in FIG. 1b, with the difference that the beam splitter 601 need not be parallel to the image producing screen 602 and/or VR/AR mirror 603. In FIG. 6a, the image producing screen 602 and VR/AR mirror 603 are substantially parallel. In FIG. 6b they are not substantially parallel. Although depicted in FIGS. 6a and 6b with the angle occurring only in the sagittal plane and with the virtual plane horizontal, any angled difference in other directions and a virtual plane at any angle may work as well. Likewise, other combinations not depicted here may be used, in which some or none of the surfaces, 601, 602 and 603 are parallel.

Figure 7A:
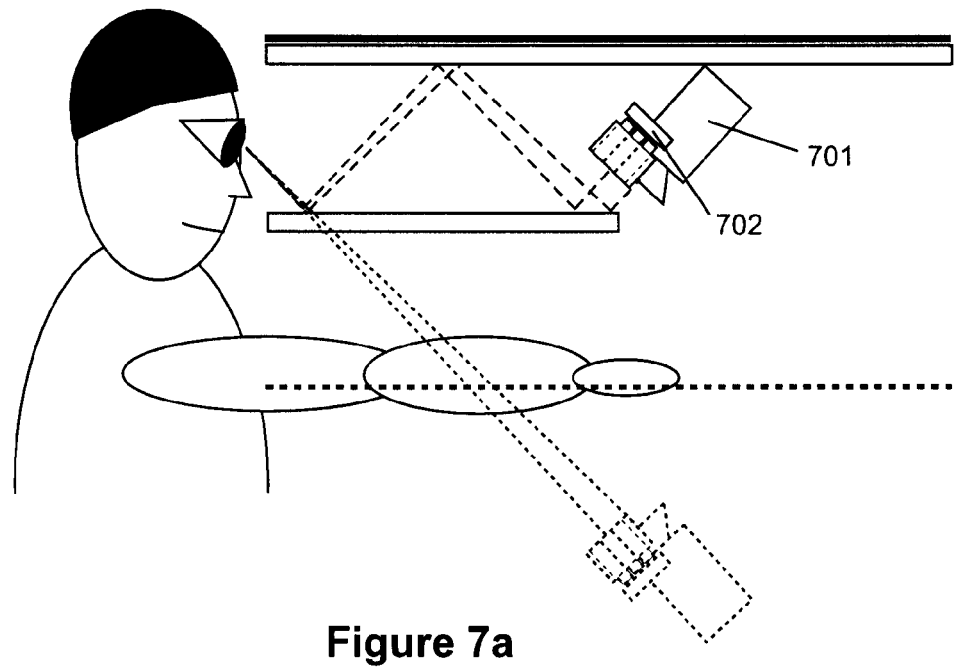
FIG. 7 shows schematic diagrams of two embodiments in which a remote gaze tracking system is integrated with VR/AR. In contrast to the embodiment shown in FIG. 1, the embodiment in FIG. 7a uses three reflections, one in the beam splitter and two in the VR/AR mirror. In the embodiment depicted in FIG. 7b there are a total of four reflections, two in each of the beam splitter and VR/AR mirror.
Figure 7B:
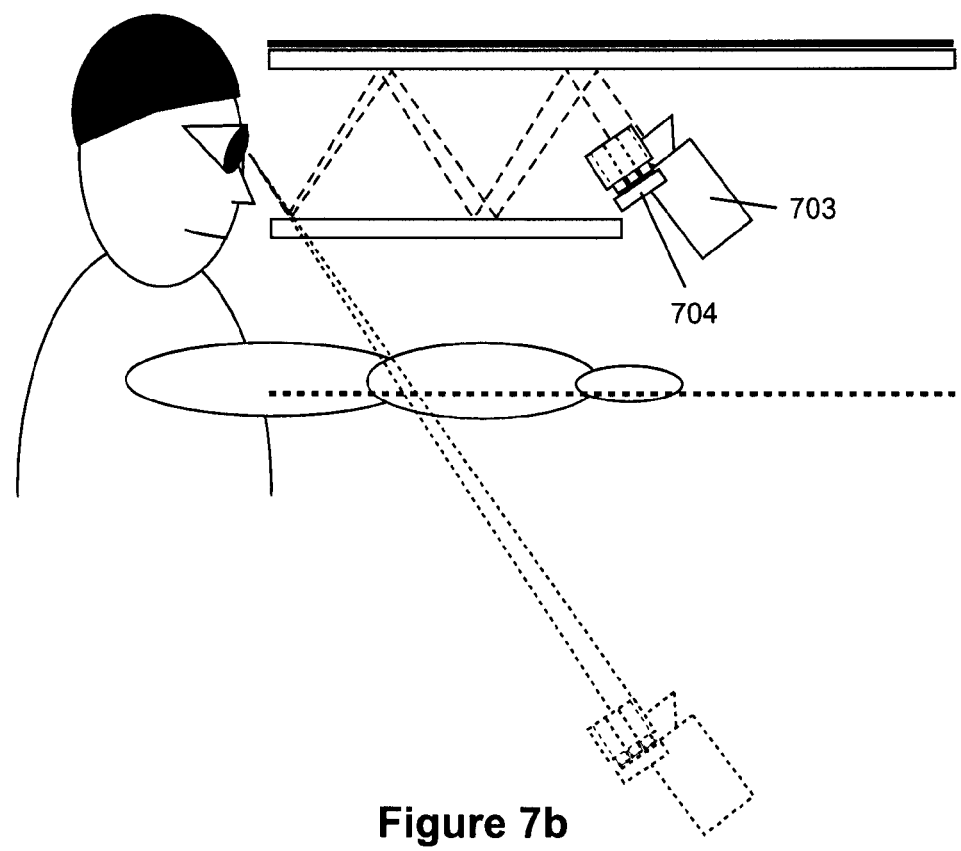
Figure 8A:
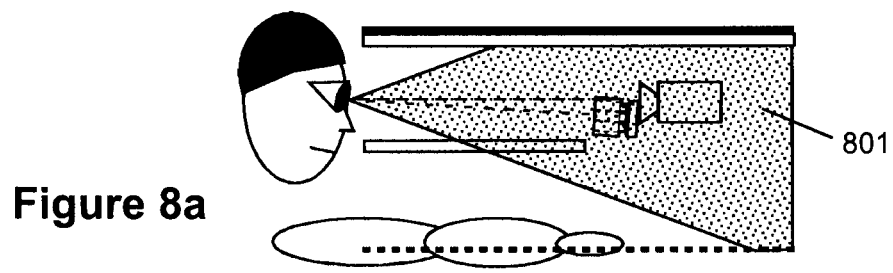
In FIG. 8a there are no reflections used: the camera and illuminator view and illuminate the eye directly.
Figure 8B:
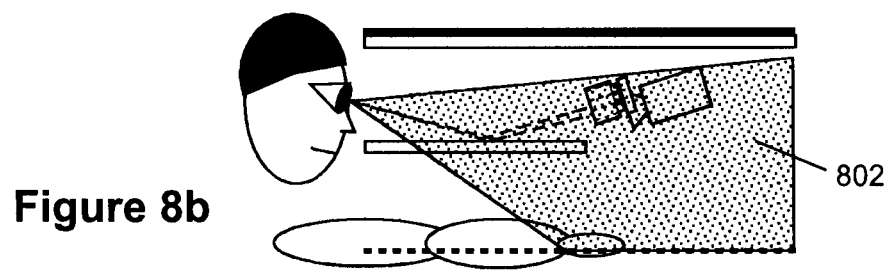
In FIGS. 8b-8e the number of reflections is 1-4 respectively.
Figure 8C:
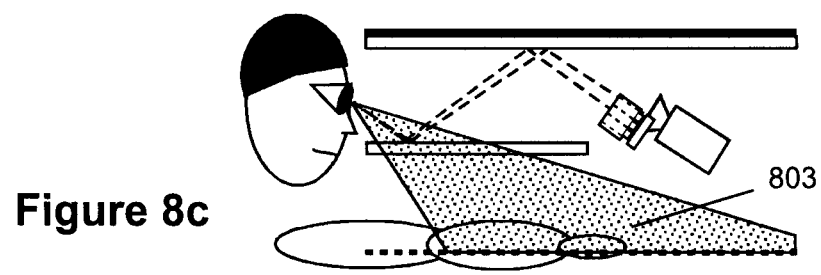
Figure 8D:
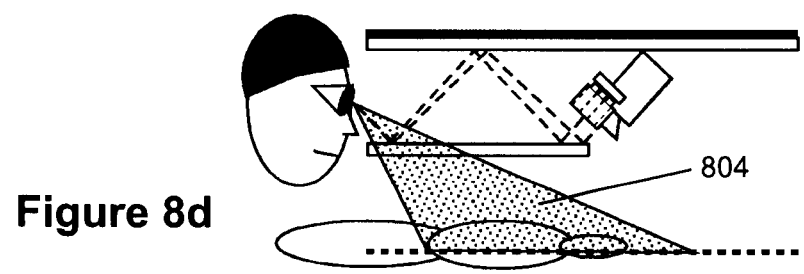
Figure 8E:
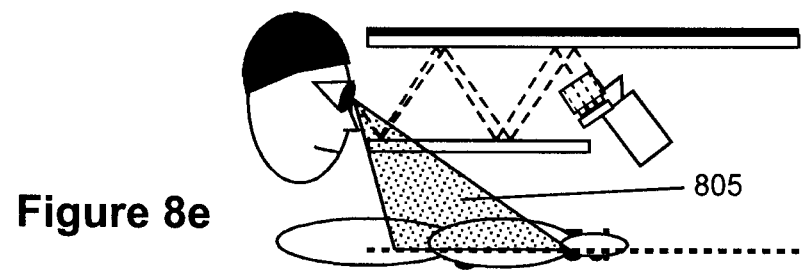

In two more embodiments, shown schematically in FIG. 7, the number of reflections that the camera and illuminator use is greater than two. In FIG. 7a the camera 701 and illuminator 702 are pointed downward to utilize three reflections: two in the VR/AR mirror and one in the beam splitter. In FIG. 7b, the camera 703 and the illuminator 704 are pointed upwards to utilize four reflections: two in the VR/AR mirror and two in the beam splitter. Other combinations may also be used, including those where the number of reflections used by the illuminator is different from those used by the camera.

Using a greater number of reflections changes the virtual location of the camera and illuminator, which changes the range of gaze angles over which gaze tracking may be carried out. As shown in FIG. 8, as the number of reflections used goes from zero in FIG. 8a to four in FIG. 8e, the range of gaze angles 801-805 over which gaze tracking may be carried out changes. Thus the desired range of gaze angles over which gaze tracking is required influences how many reflections will be required. Although each of the examples shown in FIG. 8 uses the same number of reflections for both the camera and illuminator, this does not need to be the case.

With any gaze tracking system that utilizes illumination (e.g., IR illumination), unwanted reflections (i.e., reflections that interfere with gaze tracking), such as, for example, reflections from eye glasses, may create problems. If the eye glasses are oriented at a particular angle, the reflection of the IR illuminator in the eye glasses may partially block the camera's view of the eye, preventing gaze tracking. This problem may be compounded in a head-free system where the orientation of the eye glasses changes as the user's head moves, and so the reflections cannot be controlled via standard methods that work in a head-fixed system (i.e., a system where head position is fixed), such as manually adjusting the position the illuminator or manually adjusting the angle of the eye glasses. This problem may be reduced by making the IR illuminator small (so that the reflections in the eye glasses are small), but because of minimum illumination issues, there is a limit to how small the IR illuminator can be. One solution to this problem is to use multiple cameras spatially separated from each other to simultaneously view the eye from different viewing angles. Even if the reflection blocks the view of the eye for one camera, alternate cameras arranged in this manner will have different views that may not be blocked by the reflection. Furthermore, multiple cameras typically provide the advantage of an increased range of angles over which gaze tracking may be carried out. A multiple camera approach may be used with any of the embodiments described herein. Commercially-available systems with multiple cameras, such as Smart-eye™, may be adapted for any of the embodiments described herein.

Another solution to avoid unwanted reflections is to have multiple illuminators (e.g., IR illuminators) that are spatially separated from each other, any of which may be used independently or in conjunction with other IR illuminators to illuminate the eye for gaze tracking purposes, and one or more or all of which may be independently and dynamically controlled. In particular, this implementation may use a control system to dynamically turn the IR illuminators on and off, and an algorithm implementing the control. For example, the algorithm may (i) monitor the images acquired by the camera(s) for IR reflections, (ii) determine when an IR reflection is interfering with gaze tracking, (iii) when an IR reflection is interfering with gaze tracking, identify an IR illuminator that is producing the IR reflection that is causing the interference, (iv) control which IR illuminator(s) are on and which are off to eliminate IR reflections that interfere with gaze tracking, yet retain enough IR illumination to maintain gaze tracking. Such an approach may be used with any of the embodiments described herein.

In a further embodiment, one or more additional reflecting surfaces (e.g., beam splitters) may be added to any of the embodiments described above, or any variant of the embodiments described above, to provide an additional reflection for the camera and/or illuminator. This embodiment allows the camera and/or illuminator to be located elsewhere, for example, more remotely from the subject. This may be desirable when working with subjects who are intimidated by the presence of the camera, for example, or when there are space limitations for placing the camera and/or illuminator. This embodiment is an extension of the embodiments described above in that the additional reflecting surface (e.g., a second beam splitter) is not part of the mirror-based VR or AR system, and the subject would not typically see the second beam splitter while interacting with the VR or AR environment.

Figure 9:
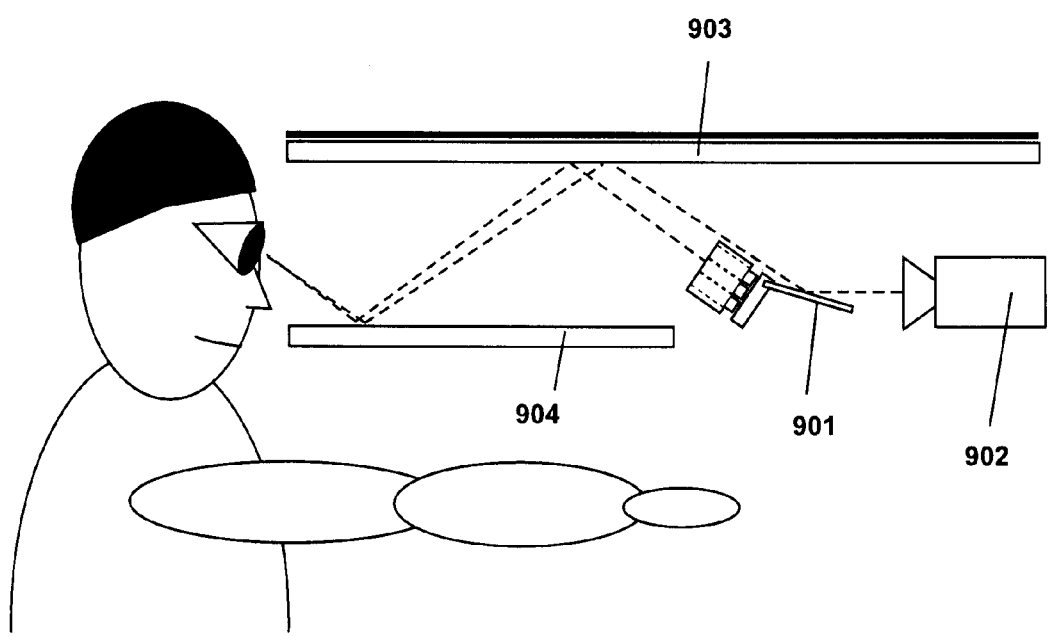
FIG. 9 is a schematic diagram of an embodiment in which a remote gaze tracking system is integrated with VR/AR. In contrast to the embodiment shown in FIG. 1, in this embodiment there is a second beam splitter that is not part of the VR/AR setup. The camera views reflections of the eye via an additional reflection in the second beam splitter.

FIG. 9 shows an example of such an embodiment, where the camera 902 views the eye via reflection in the additional reflecting surface 901 as well as via reflections in the first beam splitter 903 and VR/AR mirror 904. The additional reflecting surface 901 may be a beam splitter. In this embodiment the camera may be placed further away from the subject, as compared to the embodiment depicted in FIG. 1b. The reflecting surface 901 may also be angled to move the camera off to the side or in any other direction. The reflecting surface may also be used to change the illuminator position, instead of or in addition to changing the camera position, or multiple reflecting surfaces may be used, one each for the camera and/or illuminator.

The methods and apparatus for gaze tracking integrated with VR or AR as described herein may be used in many fields including, but not limited to, research, medical, industrial, aerospace, and entertainment applications. For example, the methods and apparatus described herein may be used in neurophysiology, in areas such as assessment, rehabilitation, and/or research involving motor function and proprioception (i.e., position sense and kinesthesia) of subjects. For example, motor function of a limb, or coordination between the limb and the eyes, may be impaired through stroke, physical injury (i.e., trauma), disease, and combinations thereof. The methods and apparatus described herein may be used for assessment, rehabilitation, and/or research of impaired motor function in such subjects, as well as to obtain baseline data for normal subjects.

Further, the methods and apparatus described herein may be combined with apparatus for determining and/or recording motion and/or position (i.e., location and/or orientation) of a subject's limb or portion thereof in 2-D or 3-D space while interacting with the VR/AR environment. The term "location" is intended to refer to a point in space. Such a point may be described within a coordinate system such a Cartesian coordinate system of 2 or 3 axes corresponding to 2- or 3-dimensional space. For a limb, a portion of interest, such as the hand, thumb, or a finger, or a joint of interest, such as the wrist, elbow, or shoulder, occupies a specific location in space at any particular time. The term "orientation" is intended to refer to the posture of a limb; that is, the relative angles in 2D or 3D space of the limb segments that result in the limb being held in a particular posture or configuration.

For example, such apparatus may include a robotic exoskeleton, such as, for example, that described in U.S. Pat. No. 6,155,993, issued 5 Dec. 2000 to Scott, an end-effector mechanical linkage, a motion capture system, or an array of two or more effectors (e.g., a touch screen, push-buttons, and the like) for determining/recording location, position, etc., of one or more portions of a limb within the VR or AR environment.

The contents of all cited publications are incorporated herein by reference in their entirety.

EQUIVALENTS

Those of ordinary skill in the art will recognize, or be able to ascertain through routine experimentation, equivalents to the embodiments described herein. Such equivalents are within the scope of the invention and are covered by the appended claims.

The invention claimed is:

1. A virtual reality (VR) or augmented reality (AR) apparatus with gaze tracking of a subject, comprising;
one or more cameras that capture images of one or both of the subject's eyes;
a display device that displays an image;

a first surface associated with the display device that at least partially reflects light from the eyes and through which the image is at least partially transmitted; and a second surface that at least partially reflects light from the eyes and receives the image and at least partially reflects the image, and renders the image to the subject as a VR or AR image in a environment;

wherein light from the subject's eyes follows a path to the one or more cameras wherein the light is at least partially reflected by the first surface one or more times, and is at least partially reflected by the second surface one or more times.

2. The apparatus of claim 1, including;
one or more illuminators that illuminate one or both of the subject's eyes;
wherein illumination from the one or more illuminators is at least partially reflected by one or both of the first and second surfaces, and then received by one or both of the subject's eyes;
wherein illumination reflected from one or both of the subject's eyes is at least partially reflected by one or both of the first and second surfaces, and then received by the one or more cameras.

3. The apparatus of claim 1, wherein the first surface is a beam splitter and second surface is a mirror or a semi-transparent mirror.

4. The apparatus of claim 2, wherein the one or more illuminators provide infra-red or near infra-red illumination.

5. The apparatus of claim 2, wherein the one or more illuminators are associated with one or more baffles;
wherein the baffles permit illumination from the illuminators to reach one or both of the subject's eyes via one or more paths;
wherein the baffles prevent illumination from the illuminators from reaching one or both of the subject's eyes via one or more alternative paths; and
wherein illumination reaching the subject's eyes permits gaze tracking of the subject.

6. The apparatus of claim 2, wherein at least one illuminator and at least one camera are located for bright pupil illumination.

7. The apparatus of claim 2, wherein at least one illuminator and at least one camera are located for dark pupil illumination.

8. The apparatus of claim 1, wherein the VR or AR image is a 3-D image.

9. The apparatus of claim 1, wherein the VR or AR image is a 2-D image.

10. The apparatus of claim 1, wherein the VR or AR image is rendered to the subject below the second surface.

11. The apparatus of claim 1, including a device that determines, records, or determines and records one or more of motion, location, and orientation of a limb or portion thereof of the subject, while the subject is interacting with the VR or AR environment with the limb or portion thereof.

12. The apparatus of claim 2, wherein
illumination from the one or more illuminators is at least partially reflected by the first surface once and by the second surface once before reaching the one or both eyes; and
illumination reflected from the subject's eye or eyes is at least partially reflected by the first surface once and by the second surface once before being received by the one or more cameras.

13. The apparatus of claim 2, wherein
illumination from the one or more illuminators is at least partially reflected by the first surface once and by the second surface twice before reaching the one or both eyes; and
illumination reflected from the subject's eye or eyes is at least partially reflected by the first surface once and by the second surface twice before being received by the one or more cameras.

14. The apparatus of claim 2, wherein
illumination from the one or more illuminators is at least partially reflected by the first surface twice and by the second surface twice before reaching the one or both eyes; and
illumination reflected from the subject's eye or eyes is at least partially reflected by the first surface twice and by the second surface twice before being received by the one or more cameras.

15. The apparatus of claim 1, wherein the first surface and the second surface are substantially parallel.

16. The apparatus of claim 1, including a third surface that at least partially reflects light following the path to the one or more cameras, or that at least partially reflects light following a path to the subject's eyes, or that at least partially reflects light following the path to the one or more cameras and at least partially reflects light following a path to the subject's eyes.

17. A method for integrating gaze tracking of a subject with virtual reality (VR) or augmented reality (AR), comprising;
providing one or more cameras that capture images of one or both of the subject's eyes;
providing a display device that displays an image;
disposing a first surface in association with the display device, that at least partially reflects light from the eyes and through which the image is at least partially transmitted;
disposing a second surface that at least partially reflects light from the eyes and receives the image and at least partially reflects the image, and renders the image to the subject as a VR or AR image in a VR or AR environment
wherein light from the subject's eyes follows a path to the one or more cameras wherein the light is at least partially reflected by the first surface one or more times, and is at least partially reflected by the second surface one or more times.

18. The method of claim 17, including;
providing one or more illuminators that illuminate one or both of the subject's eyes;
wherein illumination from the one or more illuminators is at least partially reflected by one or both of the first and second surfaces, and then received by one or both of the subject's eyes;
wherein illumination reflected from one or both of the subject's eyes is at least partially reflected by one or both of the first and second surfaces, and then received by the one or more cameras.

19. The method of claim 17, wherein the first surface is a beam splitter and second surface is a mirror or a semi-transparent mirror.

20. The method of claim 18, wherein the one or more illuminators provide infrared illumination or near-infrared illumination.

21. The method of claim 18, comprising providing one or more baffles associated with the one or more illuminators;
wherein the baffles permit illumination from the illuminators to reach one or both of the subject's eyes via one or more paths;

wherein the baffles prevent illumination from the illuminators from reaching one or both of the subject's eyes via one or more alternative paths; and wherein illumination reaching the subject's eyes permits gaze tracking of the subject.

22. The method of claim 18, comprising disposing at least one illuminator and at least one camera for bright pupil illumination.

23. The method of claim 18, comprising disposing at least one illuminator and at least one camera for dark pupil illumination.

24. The method of claim 17, comprising rendering a 3-D VR or AR image.

25. The method of claim 17, comprising rendering a 2-D VR or AR image.

26. The method of claim 17, comprising rendering the VR or AR image to the subject below the second surface.

27. The method of claim 17, further comprising determining, recording, or determining and recording one or more of motion, location, and orientation of a limb or portion thereof of the subject, while the subject is interacting with the VR or AR environment with the limb or portion thereof.

28. The method of claim 18, wherein illumination from the one or more illuminators is at least partially reflected by the first surface once and by the second surface once before reaching the one or both eyes; and illumination reflected from the subject's eye or eyes is at least partially reflected by the first surface once and by the second surface once before being received by the one or more cameras.

29. The method of claim 18, wherein illumination from the one or more illuminators is at least partially reflected by the first surface once and by the second surface twice before reaching the one or both eyes; and illumination reflected from the subject's eye or eyes is at least partially reflected by the first surface once and by the second surface twice before being received by the one or more cameras.

30. The method of claim 18, wherein illumination from the one or more illuminators is at least partially reflected by the first surface twice and by the second surface twice before reaching the one or both eyes; and illumination reflected from the subject's eye or eyes is at least partially reflected by the first surface twice and by the second surface twice before being received by the one or more cameras.

31. The method of claim 17, including disposing a third surface that at least partially reflects light following the path to the one or more cameras, or that at least partially reflects light following a path to the subject's eyes, or that at least partially reflects light following the path to the one or more cameras and at least partially reflects light following a path to the subject's eyes.

* * * * *

UNITED STATES PATENT AND TRADEMARK OFFICE
CERTIFICATE OF CORRECTION

| | | |
|---|---|---|
| PATENT NO. | : 8,730,266 B2 | Page 1 of 1 |
| APPLICATION NO. | : 13/128750 | |
| DATED | : May 20, 2014 | |
| INVENTOR(S) | : Ian E. Brown and Stephen H. Scott | |

It is certified that error appears in the above-identified patent and that said Letters Patent is hereby corrected as shown below:

In the Claims:

In Column 15, line 7, claim 1, please replace:

"or AR image in a environment;"

with

-- or AR image in a VR or AR environment; --

Signed and Sealed this
Seventh Day of October, 2014

Michelle K. Lee
*Deputy Director of the United States Patent and Trademark Office*